US 6,550,476 B1

(12) United States Patent
Ryder (10) Patent No.: US 6,550,476 B1
(45) Date of Patent: Apr. 22, 2003

(54) HEAT-MOISTURE EXCHANGER AND NEBULIZATION DEVICE

(76) Inventor: Steven L. Ryder, 2460 Hartford Ave., Fullerton, CA (US) 92835

( * ) Notice: Subject to any disclaimer, the term of this patent is extended or adjusted under 35 U.S.C. 154(b) by 0 days.

(21) Appl. No.: 09/082,665

(22) Filed: May 21, 1998

(51) Int. Cl.$^7$ .............................................. A62B 18/08

(52) U.S. Cl. ............................ 128/201.13; 128/201.25; 128/203.12; 128/203.26; 128/204.13; 128/204.17; 128/205.12

(58) Field of Search ..................... 128/201.13, 201.25, 128/203.26, 203.12, 203.25, 204.15, 204.16, 204.17, 205.12, 911, 203.22; 96/108, 124, 125, 150; 55/309, 312, 314; 165/96, 102, 103, 137, DIG. 109, DIG. 110

(56) References Cited

U.S. PATENT DOCUMENTS

| | | | | |
|---|---|---|---|---|
| 4,195,044 A | * | 3/1980 | Miller | .................. 261/142 |
| 4,200,094 A | * | 4/1980 | Gedeon et al. | ........ 128/201.13 |
| 4,391,616 A | * | 7/1983 | Imamura | ...................... 55/35 |
| 4,512,341 A | | 4/1985 | Lester | ................... 128/200.21 |
| 4,699,136 A | * | 10/1987 | Krauser | ................. 128/203.12 |
| 4,991,643 A | * | 2/1991 | Price et al. | .................... 165/38 |
| 5,008,048 A | | 4/1991 | Ryder | ........................ 261/78.2 |
| 5,109,471 A | * | 4/1992 | Lang | ......................... 392/396 |
| 5,165,392 A | | 11/1992 | Small, Jr. | |
| 5,167,679 A | * | 12/1992 | Maekawa et al. | ............. 55/208 |
| 5,226,411 A | * | 7/1993 | Levine | .................. 128/203.26 |
| 5,349,946 A | * | 9/1994 | McComb | ................ 128/203.17 |
| 5,379,760 A | | 1/1995 | Ryder | ..................... 128/203.12 |
| 5,388,574 A | * | 2/1995 | Ingebrethsen | .......... 128/203.17 |
| 5,460,172 A | | 10/1995 | Eckerbom et al. | ..... 128/201.13 |
| 5,487,382 A | | 1/1996 | Bezicot | ................. 128/207.14 |
| 5,505,768 A | | 4/1996 | Altadonna | ................... 96/108 |

(List continued on next page.)

FOREIGN PATENT DOCUMENTS

| | | |
|---|---|---|
| DE | 3513 628 C | 10/1986 |
| EP | 0 590 289 A1 | 4/1994 |
| WO | WO 98/22172 | 5/1998 |

*Primary Examiner*—Aaron J. Lewis
*Assistant Examiner*—Joseph F. Weiss, Jr.
(74) *Attorney, Agent, or Firm*—Knobbe, Martens, Olson & Bear, LLP (57) ABSTRACT

A heat-moisture exchanger (HME) and nebulization device for connection to a mechanical ventilator or anesthesia apparatus, to provide humidification or an aerosolized medication without disconnection of the HME from the ventilator circuit, a respiratory device comprising a first housing having an output fitting to provide a connection to an artificial airway of a patient, and a rotatable second housing connected to the first housing, having an input fitting to provide a connection to a ventilator circuit, the input fitting, and the output fitting are in communication with a primary gas flow, the first housing is partitioned into at least two chambers, a chamber to provide an enclosure for an absorbent material, and a chamber to provide a passageway for conveyance of an aerosol, the second housing to provide an enclosure for a nebulizer having a reservoir for a liquid medication, an instillation port to inject the liquid medication, interior to the chamber or passageway, a reciprocating member to open and close valves or having valves in linkage with the second housing, and controlled by the rotational direction of the second housing, the second housing in the horizontal orientation to position the valves to control the flow path of the primary gas flow through the chamber having the absorbent material, and control the exhaled gas flow from the patient to pass through the chamber to conserve heat and moisture, then through the ventilator circuit, rotation of the second housing to the vertical orientation to operate the nebulizer, to position the valves for the primary gas flow to entrain an aerosolized medication, and control the flow path of the primary gas flow through the passageway to bypass the absorbent material, and control the exhaled gas flow from the patient through the passageway, then through the ventilator circuit.

36 Claims, 8 Drawing Sheets

U.S. PATENT DOCUMENTS

| | | | |
|---|---|---|---|
| 5,546,930 A | 8/1996 | Wikefeldt | 128/201.13 |
| 5,577,494 A | 11/1996 | Kuypers et al. | 128/201.13 |
| 5,615,738 A * | 4/1997 | Cameron et al. | 165/103 |
| 5,662,161 A * | 9/1997 | Hughes et al. | 165/10 |
| 5,769,071 A * | 6/1998 | Turnbull | 128/203.12 |
| 5,829,428 A * | 11/1998 | Walters et al. | 128/200.24 |
| 5,916,493 A * | 6/1999 | Miller | 261/154 |
| 5,964,219 A * | 10/1999 | Pekka | 128/203.16 |
| 5,970,210 A * | 10/1999 | Anthony | 392/386 |
| 5,992,413 A * | 11/1999 | Martin, Jr. et al. | 128/201.13 |
| 6,014,972 A * | 1/2000 | Sladek | 128/203.12 |
| 6,095,135 A * | 8/2000 | Clawson et al. | 128/201.13 |
| 6,105,576 A * | 8/2000 | Clawson et al. | 128/205.12 |
| 6,470,882 B1 * | 10/2002 | Newhouse et al. | 128/200.24 |

\* cited by examiner

HEAT-MOISTURE EXCHANGER AND NEBULIZATION DEVICE

FIELD OF THE INVENTION

This invention utilized in the medical field, generally relates to an apparatus for the humidification of inspired gases and the administration of aerosolized medication in connection with mechanical ventilators, or anesthesia devices.

BACKGROUND OF THE INVENTION

Hygroscopic condensers humidifiers (HCH), heat and moisture exchangers (HME), or an artificial nose are well known in the art. These devices are routinely used for the humidification of inspired gases during mechanical ventilation.

These devices essentially work by conserving heat and moisture from the exhaled humidified gas during the exhalation phase from a patient, then recycling the heat and moisture to the subsequent inspiratory phase to humidify the dry gas from the ventilator. Recent studies have indicated, patients requiring mechanical ventilation with adequate hydration, without secretion problems, and no history of severe lung disease, can tolerate these devices for extended periods of time. Also the studies reveal, there are no increased risk of nosocomial infections with the use of these passive humidification devices, compared to heated humidification.

Due to the challenges to reduce costs in providing medical care, and as the studies have shown positive results, there is an increased acceptance and justification for the utilization of an HME.

A patient requiring mechanical ventilation with the usual method of an electronic humidification apparatus demand constant observation. For example the respiratory practitioner or nurse must assure that the reservoir of the humidifier is maintained with an adequate level of water, as well as the alarm system and heater are operating properly, and to assure a physiological proximal airway temperature.

Often the ventilator circuit must be drained from the condensation to prevent the potential drowning of a patient, and to maintain proper ventilator function. This requires often disconnecting the ventilator circuit temporarily from the patient. Another method may employ the connection of a container inline in the ventilator circuit, and a vacuum applied to remove the condensate collected in the container.

Heated wire circuits are frequently employed to reduce the amount of water condensation in the ventilator circuit. However, there is a greater cost associated with the combination of an electronic humidifier and heated wire circuit, compared to an electronic humidifier alone.

In most cases, a patient requiring mechanical ventilation will receive an aerosolized medication with a nebulizer, or metered dose inhaler (MDI). If a nebulizer is used to aerosolize a bronchodilator, the HME must be quickly removed from the ventilator circuit, and replaced with the nebulizer prefilled with a liquid medication, and "T" adaptor. After the nebulization is complete, the nebulizer and "T" adaptor are quickly disconnected, and then reattach the HME to the ventilator circuit.

If a sidestream nebulizer with "T" adaptor were connected in series in a position prior to the HME, obviously the aerosol would be filtered out, and the patient would not receive the aerosolized medication. Also, the added moisture from the aerosol would rapidly clog the HME. If the nebulizer and "T" adaptor were connected in series between the artificial airway and the HME, the patient would receive some medication, but likewise any excess aerosol would rapidly clog the HME.

The obstruction of the heat and moisture exchanging unit from the added excessive moisture will cause an increased resistance to the inspiratory gas flow, resulting in an increase work of breathing of the patient. This can have a dramatic effect on the debilitated patient, particularly during synchronous intermittent mandatory ventilation, pressure support, or spontaneous breathing with continuous positive airway pressure.

Preferably the exchange of components occurs synchronously during the brief period of time between the end of the exhalation phase, and just prior to the next inspiratory phase. The capability of the practitioner to exchange these components without interruption of ventilation, becomes increasingly more difficult with increased frequency of ventilation. If a patient is receiving continuous positive airway pressure, cessation of positive pressure occurs during the disconnection of the circuit, resulting in an intermittent drop in the intrathoracic pressure to the level of atmospheric pressure.

Obstruction of the HME device does not readily occur following a few actuations with an MDI. Therefore the HME is usually not removed prior to the use of an MDI alone. However, the HME should be removed with the combination of an MDI and spacer device, due to the added deadspace volume.

Another disadvantage of frequent disconnections of the ventilator circuit to attach a nebulizer, are the increase risk of nosocomial infections from the hospital environment, or secondary to improper hand washing technique. Moreover, the medical personnel has an increased risk of occupational hazards to the exposure of infectious airborne pathogens from a patient, such as tuberculosis, antibiotic resistant bacteria, and potential lethal viruses.

U.S. Pat. No. 5,505,568 issued to Altadonna sets forth a HUMIDITY MOISTURE EXCHANGER in which the HME having a first and second chamber, the second chamber with a pair of fluid ports. Inside the housing, is a filter or heat and moisture collecting material. To permit the uninhibited passage of aerosol from the nebulizer, the absorbent material is removed from the second chamber area, and temporarily stored within the first chamber area.

Although the device is designed to obviate the need for ventilator circuit disconnection, the device requires additional components and a nebulizer to administer an aerosol. It is unclear whether the described sealing engagement to minimize potential deadspace, could also provide an adequate seal to prevent aerosol clogging the filter, or heat and moisture collecting material when temporarily stored in the second chamber.

U.S. Pat. No. 5,546,930 issued to Wikefeldt sets forth a PATIENT CONNECTOR WITH HME, FILTER, AND NEBULIZER CONNECTION in which a Y-piece is to provide an inhalation and exhalation conduit, a patient conduit for connecting the nipple to the Y-piece, an HME disposed in the patient conduit, a nebulizer connector between the nipple and the HME, or an inhalation connector downstream to the HME for connecting the patient conduit to the nebulizer. In another embodiment a powder inhaler is also provided in connection to the nipple so that powder can be supplied to the patient.

Although Wikefeldt, has developed a method to permit the introduction of aerosols in conjunction with an HME without the interruption of mechanical ventilation, the apparatus reveals a substantial increase in the deadspace and requires several external connections of flexible tubing, and connected nebulizers. This has a disadvantage due to the increase number of connections resulting in an increased risk of potential leaks and ventilator circuit disconnection. An increase in the deadspace volume will increase the alveolar partial pressure of carbon dioxide, which could have a deleterious effect on a patient diagnosed of chronic obstructive airway disease. When an aerosolized medication is delivered by the nebulizer, a major portion of the aerosol exhaled by the patient is taken up by the HME.

While the foregoing devices are representative of the prior art, to provide an aerosolized medication in combination with an HME device, without the interruption of mechanical ventilation, which require adaptors, additional components, and nebulizers, these devices do not describe the instant invention claimed.

OBJECTS AND ADVANTAGES

Several objects and advantages of the present invention are:

(a) to provide a convenient method for the safe delivery of both humidification and aerosolization of medication with mechanical ventilators or anesthesia devices;

(b) to provide a method to maintain the continuity of a closed ventilator circuit when administering an aerosolized medication, and preventing the interruption of mechanical ventilation to a patient;

(c) to provide a method to maintain the continuity of a closed ventilator circuit, to reduce the incidence of nosocomial infections resulting from frequent disconnections of the ventilator circuit, when administering an aerosolized medication;

(d) to provide a method to maintain the continuity of a closed ventilator circuit, to reduce the exposure and occupational hazards of airborne infectious bacterial and/or viruses, from a patient to medical personnel;

(e) to provide a method to conveniently add moisture such as an aerosolized isotonic saline for the hydration of the respiratory tract, thus reducing the incidence of inpissated secretions and airway occlusion;

(f) to provide a method to reduce the number of components. Therefore reducing personnel time by eliminating the requirement to exchange components, to connect a nebulizer in a ventilator circuit with a heat and moisture exchange unit.

(g) to provide a method to deliver an aerosolized medication in conjunction with a heat and moisture exchange device, with a minimum of added deadspace volume.

SUMMARY OF THE INVENTION

In accordance with the present invention there is provided a device for both humidification and aerosolization for connection to a mechanical ventilator, or anesthesia device. The apparatus comprising of a first housing containing a material capable of absorbing heat and moisture from the exhaled air and transferring the heat and moisture to the inhaled air. A second housing for a nebulizer, is rotatable with respect to the first housing to provide an aerosol.

The first housing having an output fitting to be connected to an artificial airway of a patient. The second housing having an input fitting to be connected to a ventilator circuit and a second connection to a pressurized gas supply to the nebulizer. The first housing is partitioned into chambers. A mid chamber having at the forward end and integrated with the first housing, a flexible diaphragm.

In other embodiments the mid chamber is constructed of a separate corrugated, or flexible casing. Disposed in the mid chamber, are two sections of an absorbent material, or a heat and moisture exchanger optionally impregnated with conventional hygroscopic substances. Two chambers lateral to the mid chamber provide passageways for the conveyance of the aerosol.

Internal to the the mid chamber, and between the two sections of the absorbent material, is a reciprocating member to open and close valves. The reciprocating member is pulled backward and pushed forward by a linkage with the rotatable second housing. The linkage is provided by two pins at the rearward end of the reciprocating member, which engage two arcuate channels. Each arcuate channel is offset at an incline, having an arc length of 90 degrees, and located oppositely 180 degrees with respect to the other arcuate channel. In the forward position, the valves divert the primary gas flow or inspiratory stream to bypass the lateral chambers, to pass through the absorbent material and through the output fitting to the artificial airway. At the end of the inspiratory phase, the patient passively exhales through the output fitting, into the absorbent material to conserve heat and moisture.

When the second housing is rotated 90 degrees counterclockwise, the reciprocating member is pulled backward, by the rotation of the arcuate channels which engage the two pins. In the pulled backward position, the reciprocating member positions the valves to divert the inspiratory stream to bypass the heat and moisture exchanger, and to pass through the lateral chambers, through the output fitting, to the artificial airway of the patient. At the end of the inspiratory phase, the patient passively exhales through the output fitting, through the lateral chambers and through the ventilator circuit.

The second housing provides a reservoir for receiving a liquid, a liquid nozzle, and a gas nozzle which is supplied by a pressurized gas source by means of a pressurized gas connector, an instillation port with cap to inject a liquid medication. The second housing or nebulizer, is rotatable 90 degrees clockwise or counterclockwise on a conduit extending from the first housing. Therefore the conduit also provides an axle for the second housing. The conduit having rectangular openings are normally closed by a concentric cylindrical sleeve of the second housing. The concentric sleeve having the same sized rectangular openings, are 90 degrees out of alignment with respect to the openings of an internal conduit, to provide a rotational sleeve valve. This prevents the inspiratory stream from the ventilator escaping out of the instillation port when removing of the cap to instill the liquid medication. The closed openings on the conduit prevent back pressure regurgitation of liquid from the reservoir, and the spillage of liquid into the heat and moisture exchanger and reduction of the deadspace volume when not delivering an aerosolized medication.

In the horizontal orientation of the second housing, the reservoir is filled with an appropriate quantity of liquid medication, via the instillation port. The second housing is then rotated 90 degrees counterclockwise. The vertical orientation of the second housing will allow the liquid medication to gravitate to a region of the liquid reservoir to be aspirated and aerosolized, when the pressurized gas source has been switched on to the gas nozzle. The 90 degree counterclockwise rotation opens the rectangular openings of the conduit automatically, to allow the aerosol from the interior of the second housing to be combined with the inspiratory stream. After the aerosolization is complete, the second housing is returned to the horizontal orientation by rotating the second housing 90 degrees clockwise to resume the inspiratory stream through the heat and moisture exchanger.

The horizontal to vertical orientation of the second housing or nebulizer, is readily visualized by the medical personnel. This has the advantage to determine at a glance, whether the device is adjusted for the inspiratory stream to pass through the heat and moisture exchanger, or the device is adjusted for the inspiratory stream to deliver an aerosol, during operation of the nebulizer In another embodiment, the input fitting is equipped with a nozzle and metered dose inhaler (MDI) adaptor. In this configuration, the second housing is rotated 90 degrees counterclockwise, and the MDI is actuated in the usual manner. The reservoir of the second housing, and lateral chambers of the first housing provides a spacer device for the MDI.

In another embodiment, the mid chamber of the first housing provides a passageway for the conveyance of the aerosol, and the lateral chambers contain the heat and moisture exchange unit. Internal to the mid chamber is a reciprocating member, which is pushed forward or pulled backward by the same mechanism as described above, relative to the 90 degree clockwise and counterclockwise rotation of the second housing. The reciprocating member is comprised of a resilient material having side walls. At each end of the reciprocating member, the side walls collapse or expand to provide valves. When the second housing is in the horizontal orientation, the reciprocating member is pulled backward to provide a force to collapse the valves. This prevents the inspiratory stream from entering the mid chamber. The inspiratory stream from the ventilator by means of the internal conduit, will bypass the second housing and is directed out the openings of the mid chamber, through the heat and moisture exchange unit, to the output fitting, to the artificial airway. At the end of the inspiratory phase, the patient passively exhales through the output fitting, and through the absorbent material, to conserve heat and moisture.

The 90 degree counterclockwise rotation of the second housing in the vertical orientation pushes the reciprocating member forward. This releases the closing force on the resilient valves, and therefore the valves expand. The side walls of the reciprocating member in the forward position also closes the openings of the mid chamber. The inspiratory stream from the ventilator flowing through the second house entraining the aerosol from the interior chamber of the second housing, to bypass the heat and moisture exchange unit through the output fitting to the artificial airway. The patient passively exhales through the mid chamber through the ventilator circuit.

BRIEF DESCRIPTION OF DRAWINGS

The invention together with the further objects and advantages thereof, may be best understood by reference to the following description taken in conjunction with the accompanying drawings, in the several figures of which like reference numerals identify like elements and in which.

DETAILED DESCRIPTION OF THE INVENTION

Figure 1:
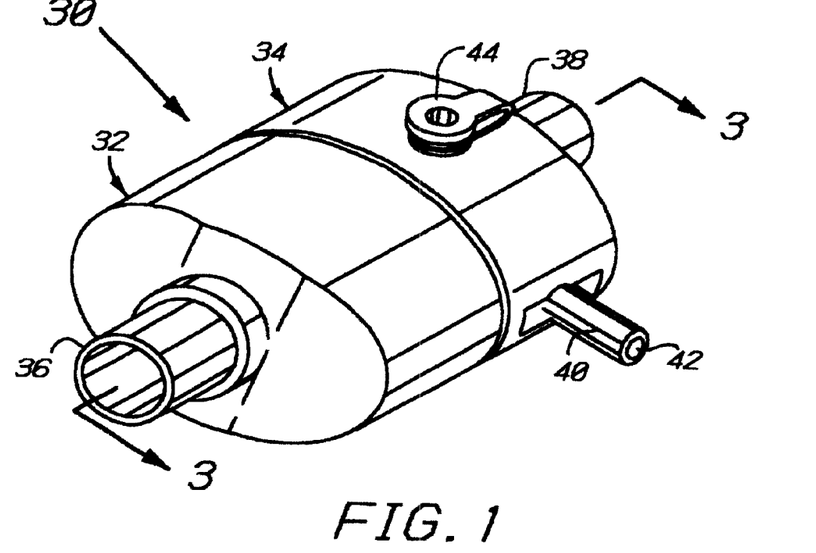
FIG. 1 is a perspective illustration of the invention.
Figure 2:
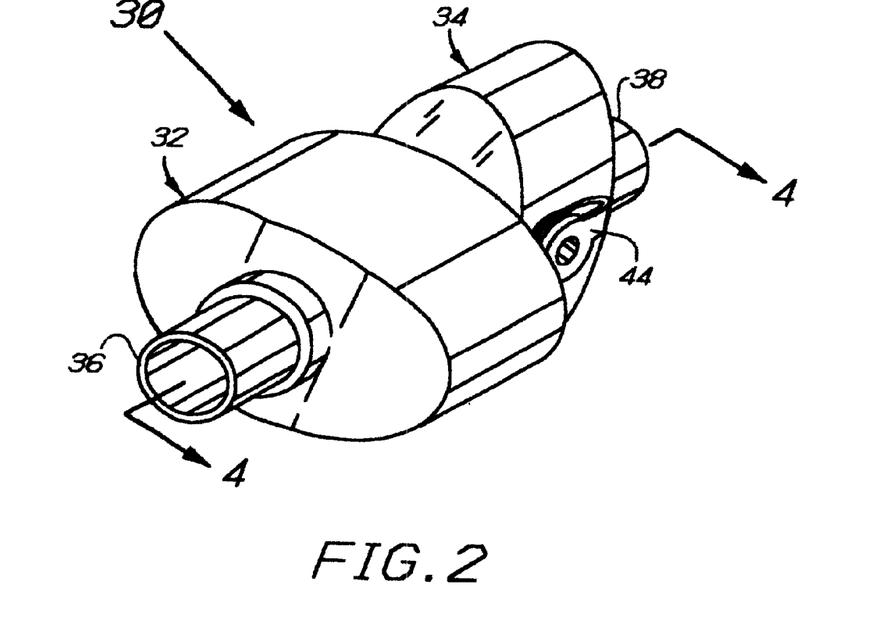
FIG. 2 is a perspective illustration of the invention, illustrating the rotational second housing.

FIG. 1 and FIG. 2, are perspective views of the heat-moisture exchanger and nebulization device constructed in accordance to the present invention, and generally referenced by numeral 30. The heat and moisture exchange unit and nebulizer includes a first housing 32 and a second rotatable housing 34. The second rotatable housing 32, further includes a generally cylindrical input fitting 38, and a generally cylindrical output fitting 36, of the first housing 34.

Second rotatable housing 34, further defines an outwardly extending pressure gas connector 40, with gas conduit 42, and a removable instillation cap 44.

Figure 3:
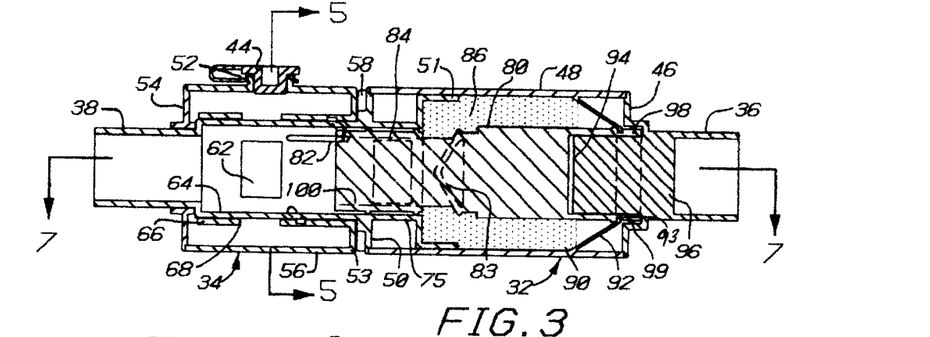
FIG. 3 is a cross sectional view taken along lines 3—3 of FIG. 1.
Figure 7:
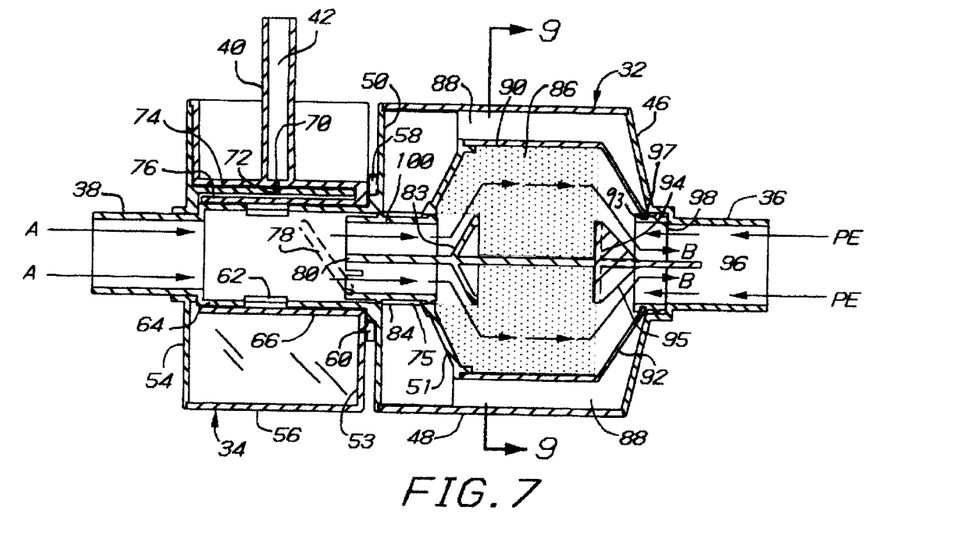
FIG. 7 is a cross sectional view taken along lines 7—7 of FIG. 3.
Figure 9:
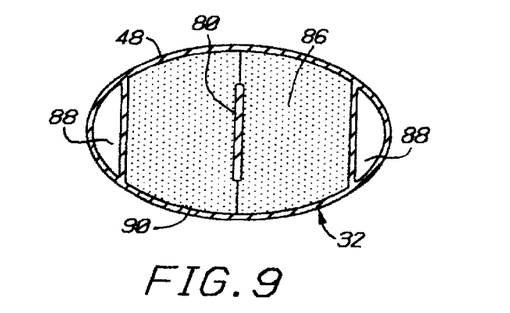
FIG. 9 is a cross sectional view taken along lines 9—9 of FIG. 7.

Referring to FIGS. 3, 7, and 9 the first housing 32 is comprised of an elliptical shell 48. The ends of the elliptical shell 48, are sealed by elliptical end wall 46, and elliptical end wall 50. The interior of the first housing is partitioned into a mid chamber 90 and lateral chambers 88. Within the mid chamber are two sections of an absorbent material 86.

Positioned between the two sections of the absorbent material is a reciprocating member 80. At the forward end on the reciprocating member 80 is a cylindrical sleeve 98. Toward the opposite end on the reciprocating member 80, a conical plug 83 and another cylindrical sleeve 100.

In the embodiment shown in FIGS. 3, 4, 7, and 8, the reciprocating member 80, elliptical end wall 46, elliptical end wall 50, and elliptical shell 48, are constructed from a resilient material such as polypropylene, by injection and blow molding methods. At the forward end of the elliptical shell 48, is a flexible diaphragm 92.

Figure 7A:
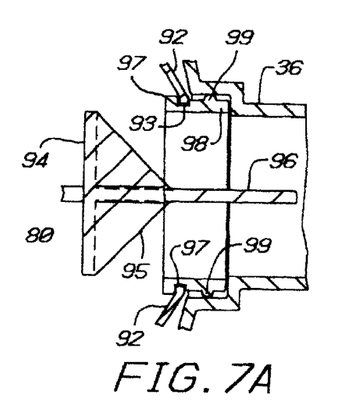
FIG. 7A is a detail enlargement of the valve sealing means illustrated in FIG. 7.

Referring to FIG. 7A, the flexible diaphragm 92 having a central aperture 97 is fitted in an annular groove 93 to join to the cylindrical sleeve 98. The ring 99 on the annular surface of the cylindrical sleeve 98 provides a seal between the cylindrical sleeve 98 and the inner diameter of the output fitting 36. The ring 99 also reduces the drag force of the seal during the backward and forward movement of the reciprocating member 80. Extending from the elliptical end wall 46, is a strut 96 which supports disc plug 94 with gussets 95.

The dimension of the outer diameter of the disc plug 94 has a dimension in close tolerance to the inner diameter dimension of the cylindrical sleeve 98. Therefore when the the reciprocating member 80 is pulled backward, the cylindrical sleeve 98 is guided by the strut 96 to the disc plug 94, to form a seal between the outer diameter of the disc plug 94, and the inner diameter of cylindrical sleeve 98.

Returning to FIGS. 3, 4, 7, and 8, the elliptical end wall 50 is comprised of a double wall. The exterior elliptical end wall 50 to seal the end of the elliptical shell 48, and the internal wall 51, to seal the end of the mid chamber 90. Between the elliptical end wall 50 and the internal wall 51, is a cylindrical passageway 75 with outlet ports 84.

Figure 3A:
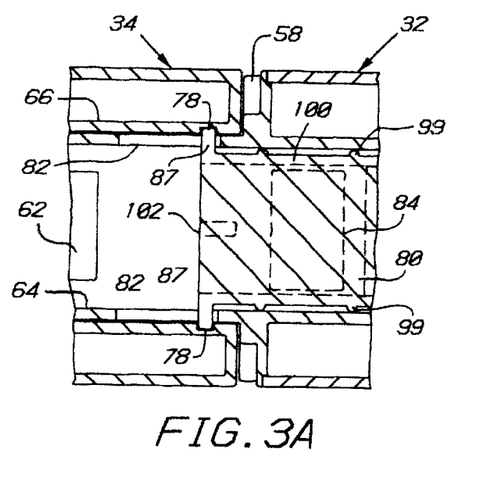
FIG. 3A is a detail enlargement of the valve sealing and thread means illustrated in FIG. 3.

Referring to FIG. 3A, at the end of the cylindrical sleeve 100 are interlocking pins 87. Each interlocking pin 87 is positioned 180 degrees relative to the other pin. The slots 82 are parallel to the reciprocating member 80, having a length to accommodate the forward and backward distance of travel of the reciprocating member 80. Each slot 82 is positioned 180 degrees relative to the other slot, in which the interlocking pins 87 project slightly through the corresponding slot 82. The notch 102 allows the interlocking pins 87 to partially bend inward on the cylindrical sleeve 100, for the conduit 64 to receive the cylindrical sleeve 100 during assembly. The concentric sleeve 66 provides two arcuate channels 78, in which the arc length of the arcuate channel 78 is equivalent to accommodate the rotation of 90 degrees of the concentric sleeve 66. The arcuate channels 78 are offset at an incline, and engage the interlocking pins 87, partially projecting through the slots 82. The engagement of the interlocking pins 87 into the arcuate channels 78, secures the rotatable second housing 34 to the conduit 64. Rotational motion of the arcuate channels 78, to provide a pull or push forward movement on the reciprocating member 80.

On the annular surface of cylindrical sleeve 100 are rings 99, to provide a seal between the cylindrical sleeve 100, and within the lumen of the cylindrical passageway 75.

Referring again to FIGS. 3, 4, 7, 8, the second housing 34 is constructed of transparent plastic, such as polystyrene or K-Resin® by injection molding methods. The second housing 34 is comprised of an elliptical shell 56 having an end wall 53, and the opposite end of elliptical shell 56, sealed by the elliptical end wall 54. The concentric sleeve 66 with sleeve inlets 68, extends from the internal end wall 53 to the end wall 54. Extending from the end wall 53, and adjacent to the concentric sleeve 66, is a projection 71. Projection 71 is comprised of two parallel plane side walls to support a plane shelf wall, having two interior right angles, with respect to the two parallel plane side walls. Central to the shelf wall, is an orifice or, gas nozzle 70. Extending outward and perpendicular from the plane shelf wall, and between the two parallel plane side walls is a pressurized gas connector 40, with a gas conduit 42 in communication with the gas nozzle 70.

Figure 6A:
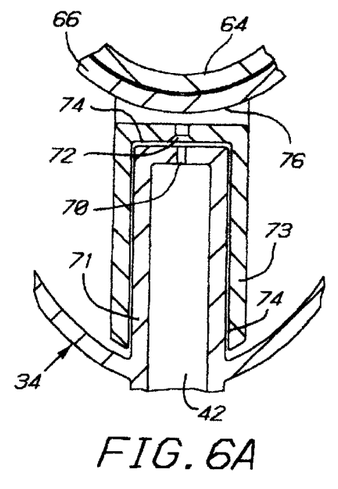
FIG. 6A is a detail enlargement of the gas and liquid nozzle means, baffle and diminutive space illustrated in FIG. 6.

Extending from the elliptical end wall 54 to the end wall 53, is projection 73. Projection 73 is a slightly larger, and analogous in structure to projection 71 having two parallel plane side walls and a plane shelf wall with respect to the two parallel plane side walls, having two interior right angles. Central to the plane shelf wall is an orifice, or liquid nozzle 72. Referring to FIG. 4A and FIG. 6A, during the assembly, the second housing 34, projection 73 from the end wall 54, slides over, to overlap projection 71 to form a diminutive space 74, and provide the concentric alignment of gas nozzle 70 with liquid nozzle 72.

The high velocity gas exiting the gas nozzle 70 passing through the liquid nozzle 72, will produce a subatmospheric pressure. The negative pressure will aspirate a liquid within the diminutive space 74, to the liquid nozzle 72. The liquid is entrained and is added into the high velocity gas exiting the gas nozzle to create an aerosol. The aerosol comprised of large and various sized liquid particles, impact on the baffle 76, of the concentric sleeve 66. This produces smaller and more uniform aerosol particle sizes.

The assembled second housing 34 is then swiveled on to the conduit 64. The arcuate channels 78 snap over the interlocking pins 87 protruding through the slots 82, preventing the removal of the the second housing 34.

Figures 4, 5, 6:
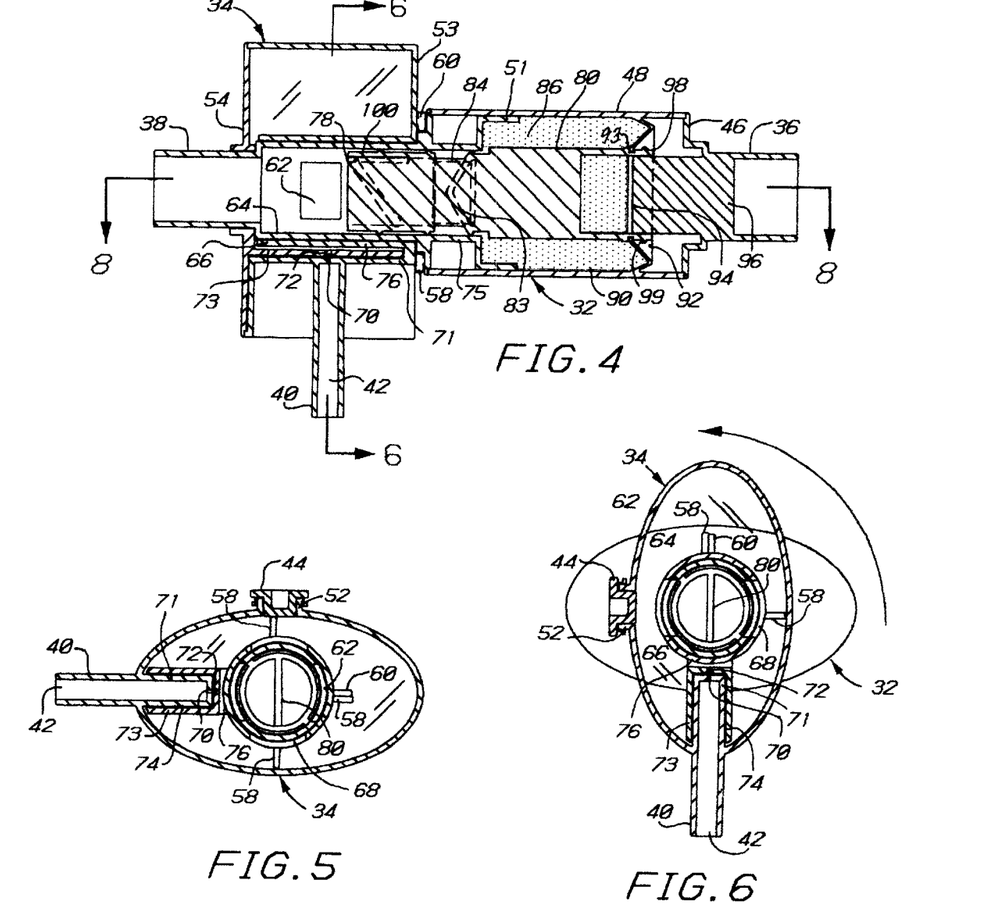
FIG. 4 is a cross sectional view taken along lines 4—4 of FIG. 2.
FIG. 5 is a cross sectional view taken along lines 5—5 of FIG. 3.
FIG. 6 is a cross sectional view taken along lines 6—6 of FIG. 4; illustrating the rotational second housing.
Figure 4A:
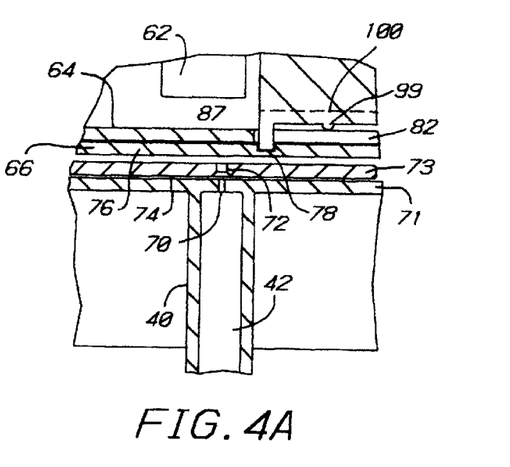
FIG. 4A is a detail enlargement of the valve sealing means illustrated in FIG. 4.

Referring to FIG. 5 and FIG. 6, extending from the elliptical end wall 50 are tabs 58, and extending from the elliptical shell with end wall 56 are tabs 60. Tabs 58, and tabs 60 provide stops to prevent rotating the second housing 34 beyond the 90 degree clockwise, or counterclockwise rotation.

In operation, the device is connected between the wye adaptor (not shown) of the ventilator circuit at the inlet fitting 38, and the artificial airway of a patient (not shown) via the output fitting 36. A flexible connecting tube (not shown) is connected from a pressurized gas source to the pressurized gas connector 40. FIG. 3, FIG. 5, and FIG. 7 illustrates the horizontal orientation of the second housing 34 with respect to the first housing 32. Referring to FIG. 7, the flow path of the primary gas flow or inspiratory stream from the ventilator is indicated from left to right by the arrows "A" through the device to arrows "B". In the horizontal orientation of the second housing 34, the concentric sleeve 66 cover and seal the inlet ports 62 of conduit 64. With the reciprocating member 80 in the forward position, the cylindrical sleeve 100 is within the cylindrical passageway 75 to seal the outlet ports 84, to prevent the primary gas flow entering the lateral chambers 88. The cylindrical sleeve 98 is within the output fitting 36, to also seal the primary gas flow from entering the lateral chambers 88. Thus providing a bypass for the inspiratory stream entering input 38, to flow through the mid chamber 90, after deflection by the conical plug 83, to pass through the heat and moisture exchange unit 86, around the disc plug 94 through the cylindrical sleeve 98, and exiting through the output fitting 36, to the artificial airway of the patient. At the end of the ventilator inspiratory cycle, the patient passively exhales designated by the exhalation flow path arrows "PE". The flow path of "PE" through the output fitting 36, into the heat and moisture exchange unit 86, and through the input fitting, then through the ventilator circuit.

In FIG. 3, and FIG. 7 to administer an aerosol, the plug 44 is first removed from the instillation port 52, with the second housing 34 in the horizontal orientation. Due to the closure of the inlet ports 62 by the concentric sleeve 66, no ventilator pressures or flows will escape out of the instillation port 52. Also the regurgitation of liquid medication out of the instillation port 52 is prevented. An appropriate quantity of liquid medication is injected into the reservoir of the second housing 34 via the instillation port 52. The plug 44 is returned and pressed fitted into the instillation port 52.

Figure 8:
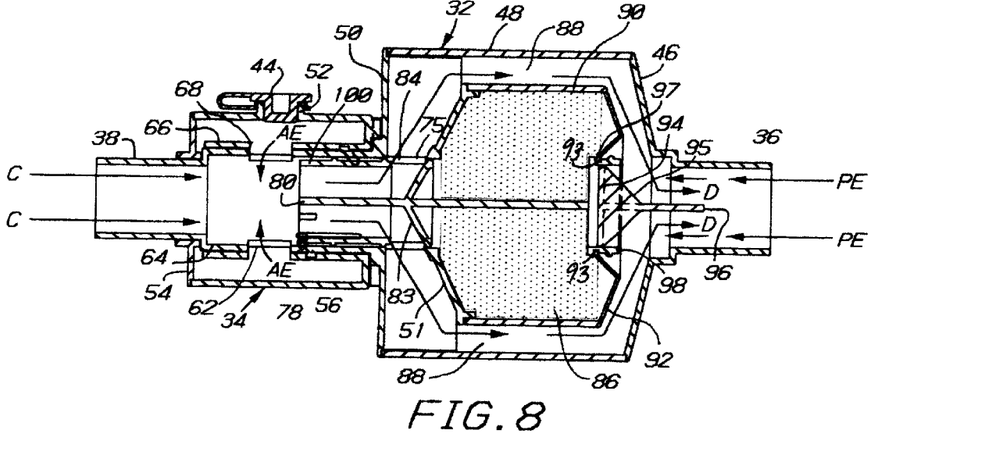
FIG. 8 is a cross sectional view taken along lines 8—8 of FIG. 4.

Referring now to FIGS. 2, 4, 6, 8, the second housing 34, or nebulizer is rotated 90 degrees to a vertical orientation. The vertical orientation of the second housing will allow the liquid medication to gravitate to the liquid reservoir. The pressurized gas source connected to the pressure gas connector 40 is switched on to generate an aerosol. In FIG. 8, the flow path of the primary gas flow or inspiratory stream is indicated from left to right by the arrows "C" through the device to arrows "D". The rotation of the second housing 34 to cause rotation of the concentric sleeve 66 to align the sleeve inlet 68 to the inlet port 62, and the rotation of the arcuate channels 78 to pull the reciprocating member 80 backward. The distance moved by the reciprocating member 80, opens the outlet ports 84 by the backward displacement of the cylindrical sleeve 100. The conical plug 83 having an outer diameter dimension in close tolerance to the inner diameter of the cylindrical passageway 75, is withdrawn within the cylindrical passageway 75 to seal and prevent the inspiratory stream from entering the mid chamber, and to divert the inspiratory stream to the lateral chambers 88. The cylindrical sleeve 98 is withdrawn to provide a seal around disc plug 94 to provide a seal to prevent the inspiratory stream to enter the mid chamber. The inspiratory stream enters input 38, to be directed through the lateral chambers 88, through the output fitting 36, to bypass the heat and moisture exchange unit 86. The opened inlet ports 62, allow for aerosol entrainment indicated by the arrows "AE" to admix with the inspiratory stream. At the end of the inspiratory cycle, the patient passively exhales indicated by the arrows "PE" through the output fitting 36, through the lateral chambers 88, through the input fitting 38, then through the ventilator circuit.

Figure 10:
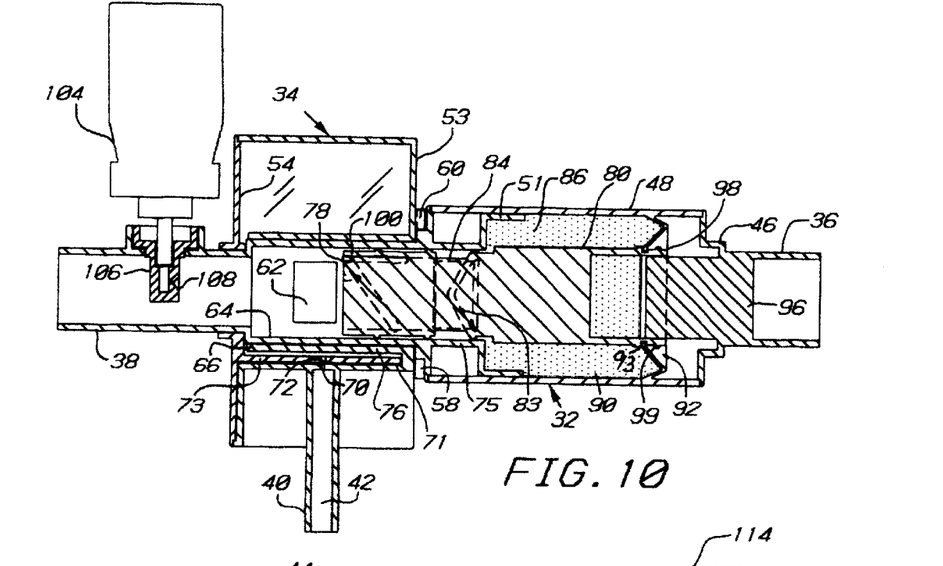
FIG. 10 is a cross sectional view taken along lines 4—4 of FIG. 2, illustrating the attachment of a metered dose inhaler container.

FIG. 10 demonstrates an optional feature of the device as an MDI spacer. The input fitting 36 is equipped with an MDI adaptor 106, having a nozzle 108. To administer an aerosolized medication with a metered dose inhaler, the second housing 34 is rotated 90 degrees counterclockwise, to the vertical orientation. The outlet stem of the MDI is placed within the MDI adaptor 106, then actuated in the usual manner, and removed after the delivery of the aerosolized medication. The second housing 34 is then rotated 90 degrees clockwise to the horizontal orientation.

FIGS. 11, 12, 13, 14, is a alternate embodiment which utilizes the novel principle of operation set forth above. In the alternate embodiment, the mid chamber is comprised of a resilient plastic material such as polypropylene to provide a corrugated mid chamber 90. The lateral chambers 88 are formed between the corrugated mid chamber 90 and the internal wall of the elliptical shell 48. Alternatively, the mid chamber 90 can also be comprised of a substantially thin polyethylene encasing(not shown), or similar plastic material. One end is sealed around the cylindrical sleeve 98. The cylindrical sleeve 98, and cylindrical sleeve 100, reciprocating member 80, conical plug 83, is injection injection molded into a unitary component.

The two sections of the open-cell material are placed into the polyethylene mid chamber 90, and sealed around the internal end wall 51. The elliptical end wall 50 with mid chamber 90 assembly, is ultrasonically welded to the elliptical shell 48, having elliptical end wall 46.

Figure 11:
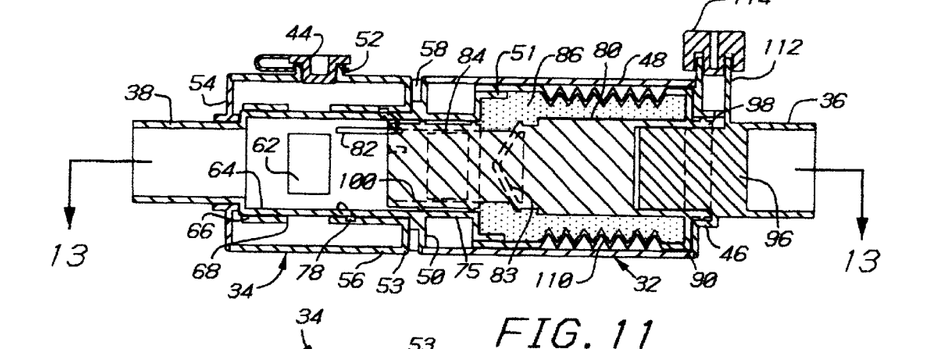
FIG. 11 is a cross sectional view of an alternate embodiment taken along lines 3—3 of FIG. 1.
Figure 12:
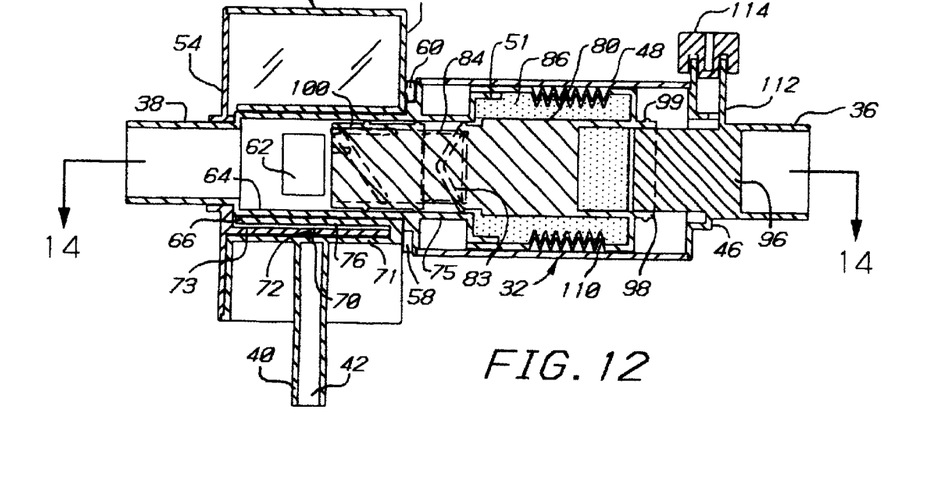
FIG. 12 is a cross sectional view of the alternate embodiment taken along lines 4—4 of FIG. 2.

In FIG. 11 and FIG. 12 is an optional socket 112 and cap 114 for the connection to a sampling tubing to monitor exhaled carbon dioxide.

Figure 13:
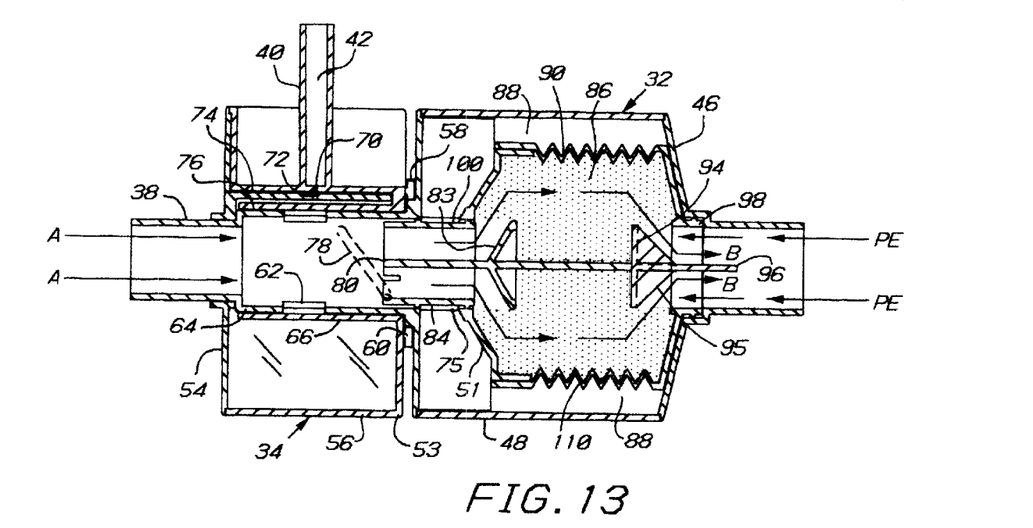
FIG. 13 is a cross sectional view of the alternate embodiment taken along lines 13—13 of FIG. 12.

Referring to FIG. 13, with the second housing 34 or nebulizer in the horizontal orientation, illustrates the position of the cylindrical sleeve 98, conical plug 83 and cylindrical sleeve 100, by the reciprocating member 80. The flow path of the inspiratory stream is indicated by arrows "A" through the device to arrows "B" to flow through the heat and moisture exchange unit 86, through the output fitting 36, to the artificial airway of the patient. The patient passively exhales indicated by arrows "PE" through the heat and moisture exchange unit 86, through the input fitting, and through the ventilator circuit.

Figure 14:
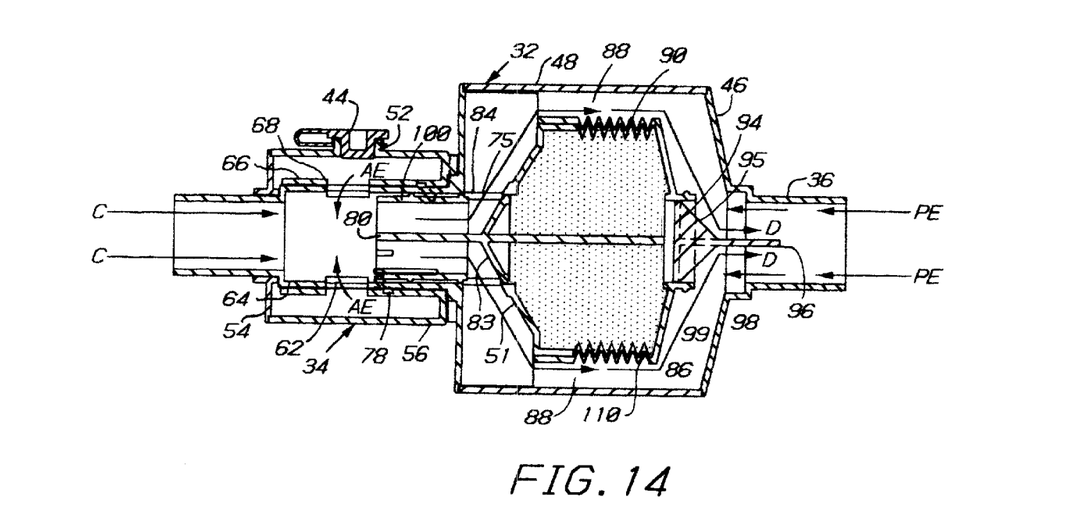
FIG. 14 is a cross sectional view of the alternate embodiment taken along lines 14—14 of FIG. 13.
Figure 15:
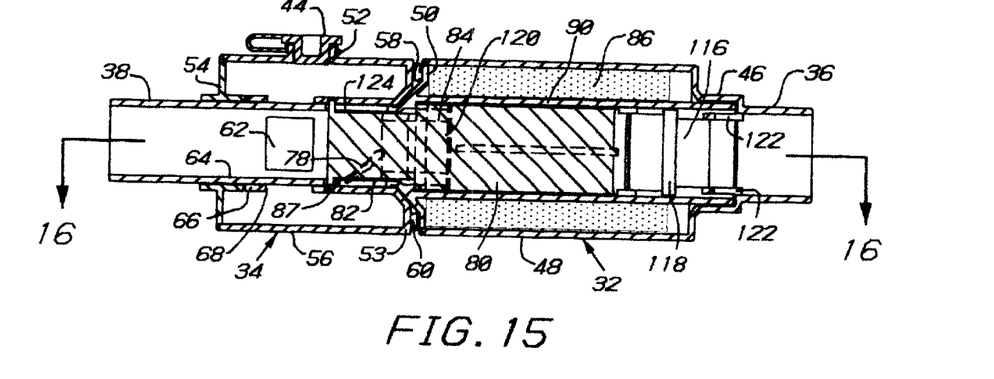
FIG. 15 is cross sectional view of an alternate embodiment taken along lines 3—3 of FIG. 1.
Figure 16:
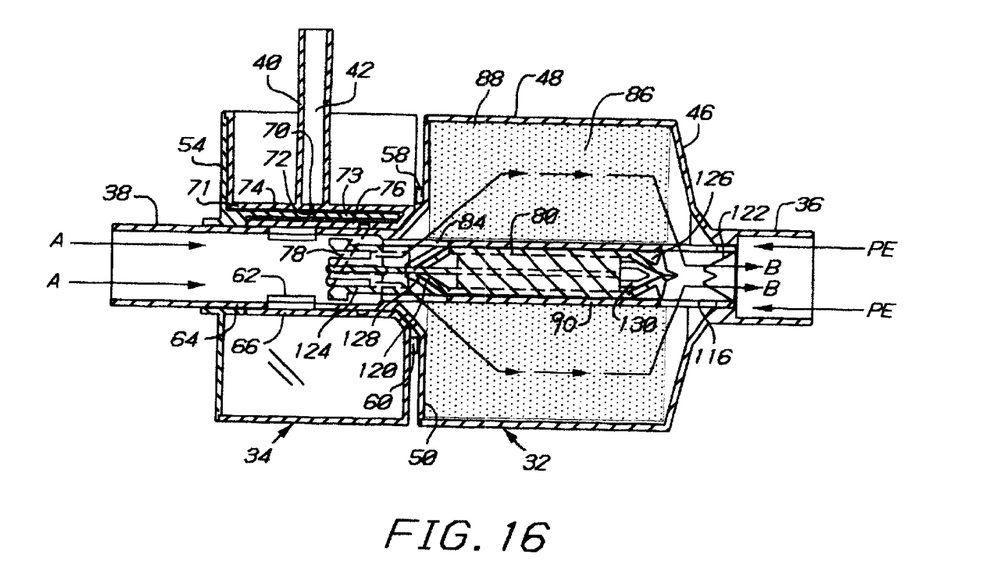
FIG. 16 is a cross sectional view of the alternate embodiment taken along lines 16—16 of FIG. 16.

In FIG. 14 the liquid medication has already been added via the instillation port 52, with plug 44 secured. The second housing 34 rotated 90 degrees counterclockwise, and the reciprocating member 80 is pulled backward by the same mechanism as previously described. The position of the cylindrical sleeve 98 is sealed around the disc plug 94, and the sealing position of the conical plug 83, and cylindrical sleeve 100, provide a bypass from the heat and moisture exchange unit. The pressurized gas source connected to the pressurized gas connector 40, is switched on to generate an aerosol. The aerosol "AE" is entrained into the inspiratory stream indicated by arrows "C" through the device to arrows "D". The inspiratory stream is directed through the lateral chambers 88, and through the output fitting 36, to the artificial airway of the patient. The patient passively exhales indicated by "PE" through the output fitting 36, through the lateral chambers 88, through the input fitting, and through the ventilator circuit.

FIGS. 15, 16, 17, 18, 19, is an alternate embodiment which utilizes the novel principle of operation set forth above. The interior of the first housing 32, is partitioned into a mid chamber 90, and lateral chambers 88. The mid chamber 90 in this configuration provides a passageway for the conveyance of an aerosol, and the lateral chambers 88 to contain the two sections of the heat and moisture exchange unit 86. Disposed in the mid chamber 90, is reciprocating member 80. The reciprocating member 80 is fabricated from a resilient material, which conforms within the internal structure of the mid chamber 90. On the opposite ends of the reciprocating member 80, are valves 118 and 120. The reciprocating member 80 is pushed forward and pulled backward in the same manner previously described.

In FIG. 15 and FIG. 16, the second housing 32 is in the horizontal orientation. Located on the floor and roof in the interior of the mid chamber 90 are beveled guides 128. As the reciprocating member 80 is pulled backward, the beveled guides 128, provide a closing force on the valves 120. At the same time the valves 118 are forced closed between the lateral tabs 126 and the internal wall of the mid chamber 90. Located on the floor and roof at the forward end of the reciprocating member 80, are beveled supports 130. The valves close against the beveled supports 130, to provide additional sealing between the valves 118, and beveled supports 130.

Referring to FIG. 16, with the second housing 34 in the horizontal orientation, with the reciprocating member 90 pulled backward, the flow path of the primary gas flow or inspiratory stream is indicated from arrows "A" through the device to arrows "B". The inlet port 62 is closed by the concentric sleeve 66. The flow of the inspiratory stream after entering the conduit 64, is prevented from entering the mid chamber 90 by the collapsed valves 120, then exiting through the outlet ports 84, through the heat and moisture exchange unit 86, through the inlet openings 116, and through the output fitting 36, to the artificial airway. At the end of the inspiratory cycle, the patient exhalation flow path indicated by arrows "PE" through the output fitting port 36. The collapsed valves 118 deflect the patient exhaled gases indicated by "PE" from the mid chamber 90, through the heat and moisture exchange unit 86 by means of the inlet openings 116, through the input fitting, and through the ventilator circuit.

Figure 17:
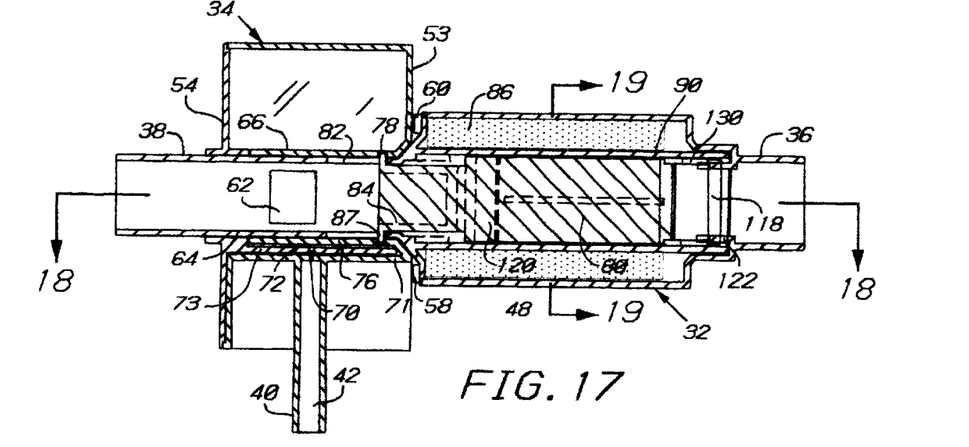
FIG. 17 is a cross sectional view of the alternate embodiment taken along lines 4—4 of FIG. 2.
Figure 18:
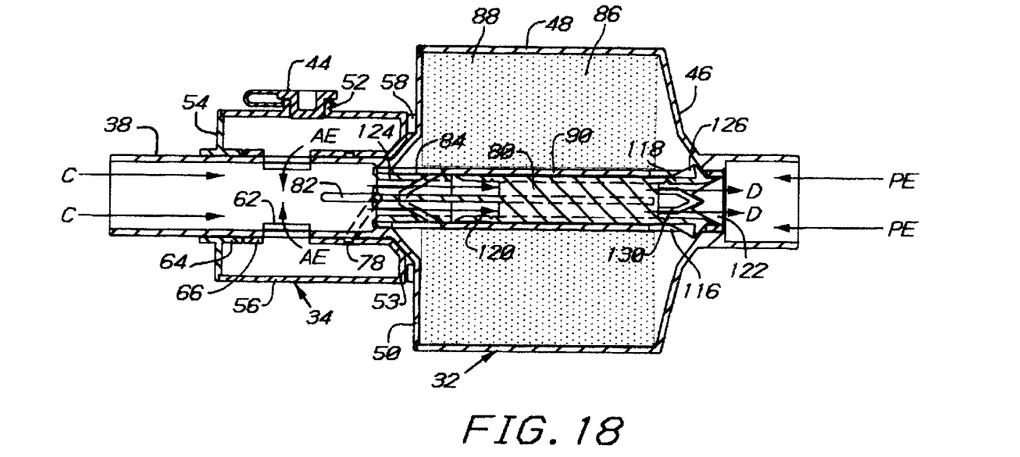
FIG. 18 is a cross sectional view of the alternate embodiment taken along lines 18—18 of FIG. 17.
Figure 19:
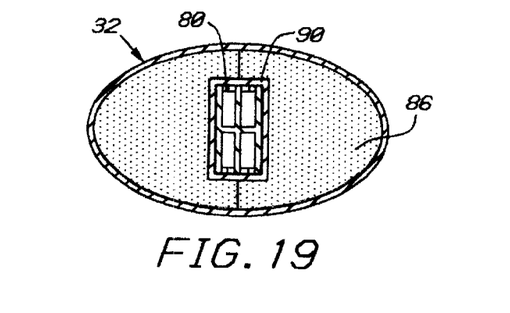
FIG. 19 is cross sectional view of the alternate embodiment taken along lines 19—19 of FIG. 17.

Referring to FIG. 17 and FIG. 18, the second housing 34 or nebulizer, is rotated 90 degrees counterclockwise, in the vertical orientation. The reciprocating member 80 is pushed forward. This releases the force on the valves 120 by the beveled guides 128, allowing the valves 118 to expand. At the same time, the force is released on the lateral tabs 126, to open the valves 120. To assure that the valves 118 are fully opened, as the reciprocating member 80 moves forward, the valves 118 are separated, and sealed between wedge support 122, and the interior wall of the output fitting 36. This provides a seal to close the inlet opening 116. Additionally, the forward displacement of the reciprocating member 80 will move the rectangular sleeve 124 to close and seal the outlet ports 84.

Referring to FIG. 18, the second housing 34 is charged with an appropriate quantity of liquid medication, in the manner previously described. The pressurized gas source is switched on to generate an aerosol. The inspiratory stream is indicated from arrows "C" through the device to arrows "D". The aerosol is entrained indicated by arrows "AE", from the inspiratory stream, via the opened inlet ports 62. Since the outlet port 84 and the inlet opening 116 are closed and sealed, the flow path of the inspiratory stream combined with the aerosol "AE", is directed through the mid chamber 90, to the output fitting 36, providing a bypass from the heat and moisture exchange unit 86. At the end of the inspiratory cycle, the patient passively exhales "PE" through the mid chamber 90, and through the ventilator circuit.

Thus, what has been shown is a heat-moisture exchanger and nebulization device, relatively simple and low cost to manufacture. To conveniently deliver an aerosolized medication with an HME. To prevent the interruption of mechanical ventilation, and eliminating potential adverse effects to the patient, and decreasing the probability of transferring microbial contamination to, or from the patient.

While particular embodiments of the invention have shown and described, it will be obvious to those skilled in the art that changes and modifications may be made without departing from the invention in its broader aspects. Therefore the aim in the appended claims is to cover all such changes and modifications as fall within the true spirit and scope of the invention.

I claim:

1. A respiratory apparatus to conserve heat and moisture from the exhaled gas in combination with an aerosol generator, comprising:

a first housing having an inlet conduit, and an outlet conduit for communication with a primary gas flow, said first housing partitioned into at least one chamber to provide an enclosure for an absorbent material and at least one passageway for the conveyance of an aerosol, a gas flow adjustment means for diverting the flow of said primary gas with said aerosol through said passageway or through said chamber comprising at least one valve and an opening for diverting the flow of said primary gas, a second housing having an inlet conduit and an outlet conduit for communication with said primary gas flow, a rotatable connecting means for connecting said second housing to said first housing, a gas nozzle communicating with the interior of said second housing having a gas connecting means for connecting to a pressurized gas supply, and a liquid nozzle in axial alignment with said gas nozzle separated therefrom by a diminutive space.

2. The apparatus of claim 1 wherein said first housing further comprises an elliptical shell having elliptical end walls, said elliptical end walls having said inlet conduit, and said outlet conduit.

3. The apparatus of claim 1 wherein said second housing further comprises an elliptical shell having elliptical end walls, said elliptical end wall shaving said inlet conduit, and said outlet conduit.

4. The apparatus of claim 1 wherein said chamber and said passageway are laterally positioned relative to each other in said first housing.

5. The apparatus of claim 1 wherein said gas flow adjustment means includes a reciprocating member cooperating with said valve, said reciprocating member having a linkage means within said rotatable connecting means, wherein rotation of said second housing actuates reciprocation of said reciprocating member with said valve to open and close said opening for selectively diverting said primary gas flow through said chamber from said passageway, or said primary gas flow and said aerosol through said passageway from said chamber.

6. The apparatus of claim 5 wherein said chamber comprises at least one diaphragm comprised of a resilient material connected to said reciprocating member.

7. The apparatus of claim 5 wherein said chamber further comprises an encasing in said first housing connected to said reciprocating member whereby reciprocation of said reciprocating member causes said encasing to reciprocate within said first housing.

8. The apparatus of claim 5 wherein said chamber comprises a flexible encasing connected to said reciprocating member having a connection means to said encasing and said gas flow adjustment means, whereby reciprocation of said reciprocating member causes said encasing to compress or expand.

9. The apparatus of claim 5 wherein said chamber comprises a flexible corrugated encasing connected to said reciprocating member whereby reciprocation of said reciprocating member causes said flexible corrugated encasing to compress or expand.

10. The apparatus of claim 1 wherein said gas flow adjustment means comprises a reciprocating member in said passageway, and a valve comprising collapsible and expansible sealing surfaces, said reciprocating member having linkage means cooperating with said rotatable connecting means within said second housing, and wherein rotation of said second housing actuates reciprocation of said reciprocating member with said valve to open and close said opening for selectively diverting said primary gas flow and said aerosol from said chamber through said passageway, or said primary gas from said passageway through said chamber.

11. The apparatus of claim 10 wherein said valve comprises a disk with a cylindrical sleeve and wherein reciprocation of said reciprocating member causes said cylindrical sleeve to move from said disk to open said valve, or causes the cylindrical sleeve to move and seal around the disk to close said valve.

12. The apparatus of claim 1 wherein said gas flow adjustment means further comprises an external cylindrical sleeve having an annular opening and an internal conduit having an annular opening, said internal conduit and said external cylindrical sleeve being disposed in said second housing and said first housing, wherein said annular opening of said external cylindrical sleeve is not aligned with said annular opening of said internal conduit in a closed condition, and wherein said opening of said external cylindrical sleeve is aligned with said opening of said internal conduit in an open condition, and whereby which said open condition and said closed condition divert said primary gas flow through said chamber from said passageway, or divert said primary gas flow and said aerosol from said chamber through said passageway.

13. The apparatus of claim 1 wherein said second housing further comprises a reservoir for holding liquid, said rotatable connecting means further comprises an internal conduit extending from said first housing to provide an axle for said second housing, said internal conduit having at least one annular opening, and an external cylindrical sleeve coaxial to said internal conduit and extending from said second housing having said outlet conduit, said external cylindrical sleeve having at least one annular opening and wherein said gas connecting means comprises a tubular member for connection to said pressurized gas supply.

14. The apparatus of claim 13, wherein flow from the pressurized gas supply through said tubular member and through said gas nozzle produces a high velocity gas flow through said liquid nozzle and induces a negative pressure to aspirate and transfer liquid from said reservoir to said liquid nozzle from said diminutive space to provide said aerosol.

15. The apparatus of claim 14 wherein said external cylindrical sleeve is spaced from said liquid nozzle to provide a baffle for said aerosol.

16. The apparatus of claim 13 further comprising a projection extending perpendicular from said second housing, said projection including said liquid nozzle and having a contour to form said diminutive space and providing said axial alignment of said gas nozzle with said liquid nozzle, and whereby said diminutive space and said liquid nozzle communicate with liquid in said reservoir.

17. The apparatus of claim 16 wherein said annular opening of said external cylindrical sleeve and said annular opening of said internal conduit are not aligned in a closed condition, and said annular opening of said external sleeve and said annular opening of said internal conduit are aligned in an open condition, and wherein rotation of said second housing and rotation of said external cylindrical sleeve on said rotatable connecting means causes alignment of said annular opening of said external cylindrical sleeve with said annular opening of said internal conduit for said open position whereby said aerosol admixes with said primary gas flow and is directed through said passageway and through said outlet conduit of said first housing.

18. The apparatus of claim 1 wherein said absorbent material comprises an open cell material.

19. The apparatus of claim 18 wherein said open cell material is impregnated with hygroscopic salts.

20. The apparatus of claim 18 wherein said open cell material comprises cellulose.

21. The apparatus of claim 18 wherein said open cell material comprises an open cell foam.

22. The apparatus of claim 1 wherein said inlet conduit of said second housing, or said inlet conduit of said first housing includes an adapter with a nozzle for a metered dose inhaler for delivering an aerosolized medication therefrom to admix with said primary gas flow.

23. The apparatus of claim 1 wherein said second housing comprises a reservoir for liquid and includes an inlet port and a cap for introducing a liquid medication to said reservoir.

24. An apparatus for selectively operating as a humidifier or a nebulizer in a respiratory or anesthesia circuit comprising, in combination:
a first housing comprising a heat and moisture exchanger said housing having a chamber containing a material for absorbing heat and moisture from exhaled gas and for delivering heat and moisture to gas to be inhaled, and a first passageway and one or more selectively operated first valves cooperating therewith for selectively bypassing said chamber;
a second housing movable relative to said first housing comprising a nebulizer for delivering an aerosol to an inspiratory gas stream and comprising a liquid holding reservoir, a liquid nozzle, a gas nozzle and a gas inlet pipe for being connected to a pressurized gas source, and a second passageway and one or more selectively operated second valves for selectively bypassing said nebulizer;
an inlet fitting for being connected to a ventilator circuit or an anesthesia circuit, an outlet fitting for being connected to a patent airway circuit, and a conduit communicating with said inlet fitting, said outlet fitting and said first and second passageways; and
a connecting assembly for movably connecting said first housing and said second housing relative to one another, and whereby said one or more first valves and said one or more second valves operate in response to movement of said first housing or said second housing relative to one another.

25. An apparatus of claim 24 wherein said inlet fitting is connected to said second housing and said outlet fitting is connected to said first housing.

26. An apparatus of claim 25 wherein said second housing is rotatable relative to said first housing.

27. An apparatus of claim 26 wherein said second housing is rotatable relative to said inlet fitting.

28. An apparatus of claim 24 wherein said first housing and said second housing are rotatable relative to one another.

29. An apparatus of claim 28 wherein said second housing is rotatable relative to said first housing.

30. An apparatus of claim 28 wherein said connecting assembly operatively connects said one or more first valves and said one or more second valves for operating said first and said second valves in response to relative movement of said first and second housing.

31. An apparatus of claim 30 wherein said connecting assembly comprises a reciprocating member cooperating with said one or more first valves and said one or more second valves.

32. An apparatus of claim 30 wherein said first and second housing are movable relative to one another between a first position wherein said one or more first valves are operated for communicating said chamber with said conduit whereby inhaled and exhaled gases pass through said chamber and wherein said one or more second valves are operated for bypassing said nebulizer, and a second position wherein said one or more first valves are operated for bypassing said chamber and wherein said one or more second valves are operated for communicating said nebulize with said conduit.

33. An apparatus of claim 32 wherein said first housing or said second housing are rotatively movable relative to one another.

34. An apparatus of claim 24 including a reciprocating member cooperating with said one or more first valves for selectively opening and closing said first passageway and selectively bypassing said chamber.

35. An apparatus of claim 24 wherein said first and second housing are movable relative to one another between a first position wherein said one or more first valves are operated for communicating said chamber with said conduit whereby inhaled and exhaled gases pass through said chamber and wherein said one or more second valves are operated for bypassing said nebulizer, and a second position wherein said one or more first valve are operated for bypassing said chamber and wherein said one or more second valves are operated for communicating said nebulizer with said conduit.

36. An apparatus of claim 35 wherein said first housing or said second housing are rotatively movable relative to one another.

* * * * *